(12) United States Patent
Frigon et al.

(10) Patent No.: US 6,741,275 B2
(45) Date of Patent: May 25, 2004

(54) LUMBER GRADING SYSTEM

(75) Inventors: Christian Frigon, Normandin (CA); Mario Gauvin, Normandin (CA)

(73) Assignee: Frigon Electrique Inc., Normandin (CA)

( * ) Notice: Subject to any disclaimer, the term of this patent is extended or adjusted under 35 U.S.C. 154(b) by 704 days.

(21) Appl. No.: 09/753,454

(22) Filed: Jan. 4, 2001

(65) Prior Publication Data

US 2002/0085093 A1 Jul. 4, 2002

(51) Int. Cl.[7] ................................................ H04N 7/18
(52) U.S. Cl. ........................................ 348/91; 356/630
(58) Field of Search ............................ 348/89, 86, 91, 348/87, 88, 92, 93–95, 130; 382/110; 378/63; 33/15; 144/347; 356/630; H04N 7/18

(56) References Cited

U.S. PATENT DOCUMENTS

| | | | | |
|---|---|---|---|---|
| 4,017,976 A | * | 4/1977 | Barr et al. ..................... 33/1 S |
| 5,325,178 A | * | 6/1994 | Louis et al. ................. 356/630 |
| 5,892,808 A | * | 4/1999 | Goulding et al. ............. 378/63 |
| 5,934,347 A | * | 8/1999 | Phelps ......................... 144/347 |
| 6,031,567 A | | 2/2000 | Johnson ........................ 348/91 |

* cited by examiner

Primary Examiner—Tung T. Vo
(74) Attorney, Agent, or Firm—McDermott, Will & Emery (57) ABSTRACT

A lumber grading system for providing a lumber cutting solution for a piece of lumber. Video acquisition circuits acquire complementary images of the sides of the piece of lumber taken by two cameras. A computer unit performs an image processing of the images and generates the lumber cutting solution for the piece of lumber based on preset grade determination parameters. The image processing involves a longitudinal division of the images of the piece of lumber into a number of consecutive zones based on predetermined lumber cutting positions, an attribution of respective grades to the zones based on an image analysis of the zones as a function of the preset grade determination parameters, and a solution search providing the lumber cutting solution as a function of the grades attributed to the zones. A communication circuit transmits the lumber cutting solution.

21 Claims, 12 Drawing Sheets

```
GRADE 1 CHARACTERISTICS              GRADE 3 CHARACTERISTICS

MAXIMUM CURVATURE         88888     MAXIMUM CURVATURE         88888
MAXIMUM % OF FALSE WOOD   88888     MAXIMUM % OF FALSE WOOD   88888
MAXIMUM % OF ROTTENNESS   88888     MAXIMUM % OF ROTTENNESS   88888
% OF KNOTS                88888     % OF KNOTS                88888
NUMBER OF CRACKS          88888     NUMBER OF CRACKS          88888

GRADE 2 CHARACTERISTICS             GRADE 4 CHARACTERISTICS

MAXIMUM CURVATURE         88888     MAXIMUM CURVATURE         88888
MAXIMUM % OF FALSE WOOD   88888     MAXIMUM % OF FALSE WOOD   88888
MAXIMUM % OF ROTTENNESS   88888     MAXIMUM % OF ROTTENNESS   88888
% OF KNOTS                88888     % OF KNOTS                88888
NUMBER OF CRACKS          88888     NUMBER OF CRACKS          88888
```

```
  GRADE 1          GRADE 2          GRADE 3          GRADE 4

VALUE 8'  8888   VALUE 8'  8888   VALUE 8'  8888   VALUE 8'  8888
VALUE 7'  8888   VALUE 7'  8888   VALUE 7'  8888   VALUE 7'  8888
VALUE 6'  8888   VALUE 6'  8888   VALUE 6'  8888   VALUE 6'  8888
VALUE 5'  8888   VALUE 5'  8888   VALUE 5'  8888   VALUE 5'  8888
VALUE 4'  8888   VALUE 4'  8888   VALUE 4'  8888   VALUE 4'  8888
```

84

VALUE CHOICE          ☐
WOOD RECOVERY CHOICE  ☐    } 86

| ZONES | GRADE IN THE ZONES | | | | | | | |
|---|---|---|---|---|---|---|---|---|
| | 1 | 2 | 3 | 4 | 5 | 6 | 7 | 8 |
| 8 FEET GRADE 1 | 1 | 1 | 1 | 1 | 1 | 1 | 1 | 1 |
| 8 FEET GRADE 2 | 1 | 1 | 1 | 1 | 1 | 1 | 1 | |
| | 1 | 1 | 1 | 1 | 1 | 1 | 1 | 2 |
| | 1 | 1 | 1 | 1 | 1 | 2 | 2 | 1 OR 2 |
| | 1 | 1 | 1 | 2 | 1 OR 2 | 1 OR 2 | 1 OR 2 | 1 OR 2 |
| | 1 | 1 | 2 | 1 OR 2 | 1 OR 2 | 1 OR 2 | 1 OR 2 | 1 OR 2 |
| | 1 | 2 | 1 OR 2 | 1 OR 2 | 1 OR 2 | 1 OR 2 | 1 OR 2 | 1 OR 2 |
| | 2 | 1 OR 2 | 1 OR 2 | 1 OR 2 | 1 OR 2 | 1 OR 2 | 1 OR 2 | 1 OR 2 |
| 8 FEET GRADE 3 | 1 OR 2 | 1 OR 2 | 1 OR 2 | 1 OR 2 | 1 OR 2 | 1 OR 2 | 1 OR 2 | 3 |
| | 1 OR 2 | 1 OR 2 | 1 OR 2 | 1 OR 2 | 1 OR 2 | 3 | 3 | 1-2 OR 3 |
| | 1 OR 2 | 1 OR 2 | 1 OR 2 | 1 OR 2 | 3 | 1-2 OR 3 | 1-2 OR 3 | 1-2 OR 3 |
| | 1 OR 2 | 1 OR 2 | 1 OR 2 | 3 | 1-2 OR 3 | 1-2 OR 3 | 1-2 OR 3 | 1-2 OR 3 |
| | 1 OR 2 | 1 OR 2 | 3 | 1-2 OR 3 | 1-2 OR 3 | 1-2 OR 3 | 1-2 OR 3 | 1-2 OR 3 |
| | 1 OR 2 | 3 | 1-2 OR 3 | 1-2 OR 3 | 1-2 OR 3 | 1-2 OR 3 | 1-2 OR 3 | 1-2 OR 3 |
| | 3 | 1-2 OR 3 | 1-2 OR 3 | 1-2 OR 3 | 1-2 OR 3 | 1-2 OR 3 | 1-2 OR 3 | 1-2 OR 3 |
| 8 FEET GRADE 4 | 1-2 OR 3 | 1-2 OR 3 | 1-2 OR 3 | 1-2 OR 3 | 1-2 OR 3 | 1-2 OR 3 | 1-2 OR 3 | 4 |
| | 1-2 OR 3 | 1-2 OR 3 | 1-2 OR 3 | 1-2 OR 3 | 1-2 OR 3 | 4 | 4 | 1-2-3 OR 4 |
| | 1-2 OR 3 | 1-2 OR 3 | 1-2 OR 3 | 1-2 OR 3 | 4 | 1-2-3 OR 4 | 1-2-3 OR 4 | 1-2-3 OR 4 |
| | 1-2 OR 3 | 1-2 OR 3 | 1-2 OR 3 | 4 | 1-2-3 OR 4 | 1-2-3 OR 4 | 1-2-3 OR 4 | 1-2-3 OR 4 |
| | 1-2 OR 3 | 1-2 OR 3 | 4 | 1-2-3 OR 4 | 1-2-3 OR 4 | 1-2-3 OR 4 | 1-2-3 OR 4 | 1-2-3 OR 4 |
| | 1-2 OR 3 | 4 | 1-2-3 OR 4 | 1-2-3 OR 4 | 1-2-3 OR 4 | 1-2-3 OR 4 | 1-2-3 OR 4 | 1-2-3 OR 4 |
| | 4 | 1-2-3 OR 4 | 1-2-3 OR 4 | 1-2-3 OR 4 | 1-2-3 OR 4 | 1-2-3 OR 4 | 1-2-3 OR 4 | 1-2-3 OR 4 |

FIG. 7B

| ZONES | GRADE IN THE ZONES | | | | | | | |
|---|---|---|---|---|---|---|---|---|
|  | 1 | 2 | 3 | 4 | 5 | 6 | 7 | 8 |
| 7 FEET GRADE 1 REMOTE END | 1 | 1 | 1 | 1 | 1 | 1 | 1 | ** |
| 7 FEET GRADE 1 NEAR END | ** |  |  |  |  |  |  | 1 |
| 7 FEET GRADE 2 REMOTE END | 1 | 1 | 1 | 1 | 1 | 1 | 2 | ** |
|  | 1 | 1 | 1 | 1 | 1 | 2 | 1 OR 2 | ** |
|  | 1 | 1 | 1 | 2 | 2 | 1 OR 2 | 1 OR 2 | ** |
|  | 1 | 2 | 2 | 1 OR 2 | 1 OR 2 | 1 OR 2 | 1 OR 2 | ** |
|  | 2 | 1 OR 2 | 1 OR 2 | 1 OR 2 | 1 OR 2 | 1 OR 2 | 1 OR 2 | ** |
| 7 FEET GRADE 2 NEAR END | ** | 1 OR 2 | 1 | 1 | 1 | 1 | 1 | 1 |
|  | ** | 1 OR 2 | 2 | 2 | 1 | 1 | 1 | 1 |
|  | ** | 1 OR 2 | 1 OR 2 | 1 OR 2 | 2 | 1 | 1 | 1 |
|  | ** | 1 OR 2 | 1 OR 2 | 1 OR 2 | 1 OR 2 | 2 | 1 | 1 |
|  | ** | 1 OR 2 | 1 OR 2 | 1 OR 2 | 1 OR 2 | 1 OR 2 | 2 | 1 |
|  | ** | 1 OR 2 | 1 OR 2 | 1 OR 2 | 1 OR 2 | 1 OR 2 | 1 OR 2 | 2 |
| 7 FEET GRADE 3 REMOTE END | 1 OR 2 | 1 OR 2 | 1 OR 2 | 1 OR 2 | 1 OR 2 | 1 OR 2 | 1 OR 2 | ** |
|  | 1 OR 2 | 1 OR 2 | 1 OR 2 | 1 OR 2 | 1 OR 2 | 1 OR 2 | 1 OR 2 | ** |
|  | 1 OR 2 | 1 OR 2 | 1 OR 2 | 1 OR 2 | 1 OR 2 | 1 OR 2 | 1 OR 2 | ** |
|  | 1 OR 2 | 1 OR 2 | 1 OR 2 | 1 OR 2 | 1 OR 2 | 1 OR 2 | 1 OR 2 | ** |
|  | 1 OR 2 | 1 OR 2 | 1 OR 2 | 1 OR 2 | 1 OR 2 | 1 OR 2 | 1 OR 2 | ** |
|  | 1 OR 2 | 3 | 3 | 3 | 3 | 3 | 3 | ** |
|  | 3 | 1-2 OR 3 | 1-2 OR 3 | 1-2 OR 3 | 1-2 OR 3 | 1-2 OR 3 | 1-2 OR 3 | ** |

FIG. 7C

| ZONES | GRADE IN THE ZONES | | | | | | | |
|---|---|---|---|---|---|---|---|---|
| | 1 | 2 | 3 | 4 | 5 | 6 | 7 | 8 |
| 7 FEET GRADE 3 NEAR END | ** | 3 | 1 OR 2 | 1 OR 2 | 1 OR 2 | 1 OR 2 | 1 OR 2 | 1 OR 2 |
| | ** | 1-2 OR 3 | 3 | 1 OR 2 | 1 OR 2 | 1 OR 2 | 1 OR 2 | 1 OR 2 |
| | ** | 1-2 OR 3 | 1-2 OR 3 | 3 | 1 OR 2 | 1 OR 2 | 1 OR 2 | 1 OR 2 |
| | ** | 1-2 OR 3 | 1-2 OR 3 | 1-2 OR 3 | 3 | 1 OR 2 | 1 OR 2 | 1 OR 2 |
| | ** | 1-2 OR 3 | 1-2 OR 3 | 1-2 OR 3 | 1-2 OR 3 | 3 | 1 OR 2 | 1 OR 2 |
| | ** | 1-2 OR 3 | 1-2 OR 3 | 1-2 OR 3 | 1-2 OR 3 | 1-2 OR 3 | 3 | 1 OR 2 |
| | ** | 1-2 OR 3 | 1-2 OR 3 | 1-2 OR 3 | 1-2 OR 3 | 1-2 OR 3 | 1-2 OR 3 | 3 |
| 7 FEET GRADE 4 REMOTE END | 1-2 OR 3 | 1-2 OR 3 | 1-2 OR 3 | 1-2 OR 3 | 1-2 OR 3 | 1-2 OR 3 | 4 | ** |
| | 1-2 OR 3 | 1-2 OR 3 | 1-2 OR 3 | 1-2 OR 3 | 1-2 OR 3 | 4 | 1-2-3 OR 4 | ** |
| | 1-2 OR 3 | 1-2 OR 3 | 1-2 OR 3 | 1-2 OR 3 | 4 | 1-2-3 OR 4 | 1-2-3 OR 4 | ** |
| | 1-2 OR 3 | 1-2 OR 3 | 1-2 OR 3 | 4 | 1-2-3 OR 4 | 1-2-3 OR 4 | 1-2-3 OR 4 | ** |
| | 1-2 OR 3 | 1-2 OR 3 | 4 | 1-2-3 OR 4 | 1-2-3 OR 4 | 1-2-3 OR 4 | 1-2-3 OR 4 | ** |
| | 1-2 OR 3 | 4 | 1-2-3 OR 4 | 1-2-3 OR 4 | 1-2-3 OR 4 | 1-2-3 OR 4 | 1-2-3 OR 4 | ** |
| | 4 | 1-2-3 OR 4 | 1-2-3 OR 4 | 1-2-3 OR 4 | 1-2-3 OR 4 | 1-2-3 OR 4 | 1-2-3 OR 4 | ** |
| 7 FEET GRADE 4 NEAR END | ** | 1-2 OR 3 | 1-2 OR 3 | 1-2 OR 3 | 1-2 OR 3 | 1-2 OR 3 | 1-2 OR 3 | 4 |
| | ** | 1-2 OR 3 | 1-2 OR 3 | 1-2 OR 3 | 1-2 OR 3 | 1-2 OR 3 | 4 | 1-2-3 OR 4 |
| | ** | 1-2 OR 3 | 1-2 OR 3 | 1-2 OR 3 | 1-2 OR 3 | 4 | 1-2-3 OR 4 | 1-2-3 OR 4 |
| | ** | 1-2 OR 3 | 1-2 OR 3 | 1-2 OR 3 | 4 | 1-2-3 OR 4 | 1-2-3 OR 4 | 1-2-3 OR 4 |
| | ** | 1-2 OR 3 | 1-2 OR 3 | 4 | 1-2-3 OR 4 | 1-2-3 OR 4 | 1-2-3 OR 4 | 1-2-3 OR 4 |
| | ** | 1-2 OR 3 | 4 | 1-2-3 OR 4 | 1-2-3 OR 4 | 1-2-3 OR 4 | 1-2-3 OR 4 | 1-2-3 OR 4 |
| | ** | 4 | 1-2-3 OR 4 | 1-2-3 OR 4 | 1-2-3 OR 4 | 1-2-3 OR 4 | 1-2-3 OR 4 | 1-2-3 OR 4 |

FIG. 7D

| ZONES | GRADE IN THE ZONES | | | | | | | |
|---|---|---|---|---|---|---|---|---|
| | 1 | 2 | 3 | 4 | 5 | 6 | 7 | 8 |
| 6 FEET GRADE 1 REMOTE END | 1 | 1 | 1 | 1 | 1 | 1 | ** | ** |
| 6 FEET GRADE 1 NEAR END | ** | ** | 1 | 1 | 1 | 1 | 1 | 1 |
| 6 FEET GRADE 2 REMOTE END | 1 | 1 | 1 | 1 | 1 | 2 | ** | ** |
| | 1 | 1 | 1 | 1 | 2 | 1 OR 2 | ** | ** |
| | 1 | 1 | 2 | 2 | 1 OR 2 | 1 OR 2 | ** | ** |
| | 1 | 2 | 1 OR 2 | 1 OR 2 | 1 OR 2 | 1 OR 2 | ** | ** |
| | 2 | 1 OR 2 | 1 OR 2 | 1 OR 2 | 1 OR 2 | 1 OR 2 | ** | ** |
| 6 FEET GRADE 3 REMOTE END | 1 OR 2 | 1 OR 2 | 1 OR 2 | 1 OR 2 | 1 OR 2 | 3 | ** | ** |
| | 1 OR 2 | 1 OR 2 | 1 OR 2 | 1 OR 2 | 3 | 1-2 OR 3 | ** | ** |
| | 1 OR 2 | 1 OR 2 | 1 OR 2 | 3 | 1-2 OR 3 | 1-2 OR 3 | ** | ** |
| | 1 OR 2 | 1 OR 2 | 3 | 1-2 OR 3 | 1-2 OR 3 | 1-2 OR 3 | ** | ** |
| | 1 OR 2 | 3 | 1-2 OR 3 | 1-2 OR 3 | 1-2 OR 3 | 1-2 OR 3 | ** | ** |
| | 3 | 1-2 OR 3 | 1-2 OR 3 | 1-2 OR 3 | 1-2 OR 3 | 1-2 OR 3 | ** | ** |
| 6 FEET GRADE 4 REMOTE END | 1-2 OR 3 | 1-2 OR 3 | 1-2 OR 3 | 1-2 OR 3 | 1-2 OR 3 | 4 | ** | ** |
| | 1-2 OR 3 | 1-2 OR 3 | 1-2 OR 3 | 1-2 OR 3 | 4 | 1-2-3 OR 4 | ** | ** |
| | 1-2 OR 3 | 1-2 OR 3 | 1-2 OR 3 | 4 | 1-2-3 OR 4 | 1-2-3 OR 4 | ** | ** |
| | 1-2 OR 3 | 1-2 OR 3 | 4 | 1-2-3 OR 4 | 1-2-3 OR 4 | 1-2-3 OR 4 | ** | ** |
| | 1-2 OR 3 | 4 | 1-2-3 OR 4 | 1-2-3 OR 4 | 1-2-3 OR 4 | 1-2-3 OR 4 | ** | ** |
| | 4 | 1-2-3 OR 4 | 1-2-3 OR 4 | 1-2-3 OR 4 | 1-2-3 OR 4 | 1-2-3 OR 4 | ** | ** |

FIG. 7E

| ZONES | GRADE IN THE ZONES | | | | | | | |
|---|---|---|---|---|---|---|---|---|
| | 1 | 2 | 3 | 4 | 5 | 6 | 7 | 8 |
| 5 FEET GRADE 1 REMOTE END | 1 | 1 | 1 | 1 | 1 | *.* | | |
| 5 FEET GRADE 2 REMOTE END | 1 | 1 | 1 | 1 | 2 | *.* | *.* | *.* |
| | 1 | 1 | 2 | 2 | 1 OR 2 | *.* | *.* | *.* |
| | 1 | 1 OR 2 | 1 OR 2 | 1 OR 2 | 1 OR 2 | *.* | *.* | *.* |
| | 1 | 1 OR 2 | 1 OR 2 | 1 OR 2 | 1 OR 2 | *.* | *.* | *.* |
| | 2 | 1 OR 2 | 1 OR 2 | 1 OR 2 | 1 OR 2 | *.* | *.* | *.* |
| 5 FEET GRADE 3 REMOTE END | 1 OR 2 | 1 OR 2 | 3 | 3 | 3 | *.* | *.* | *.* |
| | 1 OR 2 | 1 OR 2 | 1-2 OR 3 | 1-2 OR 3 | 1-2 OR 3 | *.* | *.* | *.* |
| | 1 OR 2 | 1 OR 2 | 1-2 OR 3 | 1-2 OR 3 | 1-2 OR 3 | *.* | *.* | *.* |
| | 1 OR 2 | 1 OR 2 | 1-2 OR 3 | 1-2 OR 3 | 1-2 OR 3 | *.* | *.* | *.* |
| | 3 | 1-2 OR 3 | 1-2 OR 3 | 1-2 OR 3 | 1-2 OR 3 | *.* | *.* | *.* |
| 5 FEET GRADE 4 REMOTE END | 1-2 OR 3 | 1-2 OR 3 | 1-2 OR 3 | 1-2 OR 3 | 4 | *.* | *.* | *.* |
| | 1-2 OR 3 | 1-2 OR 3 | 4 | 4 | 1-2-3 OR 4 | *.* | *.* | *.* |
| | 1-2 OR 3 | 1-2 OR 3 | 1-2-3 OR 4 | 1-2-3 OR 4 | 1-2-3 OR 4 | *.* | *.* | *.* |
| | 1-2 OR 3 | 1-2 OR 3 | 1-2-3 OR 4 | 1-2-3 OR 4 | 1-2-3 OR 4 | *.* | *.* | *.* |
| | 4 | 1-2-3 OR 4 | 1-2-3 OR 4 | 1-2-3 OR 4 | 1-2-3 OR 4 | *.* | *.* | *.* |

AND SO ON...    *.* = REJECT

FIG. 8A

| ZONE | 1 | 2 | 3 | 4 | 5 | 6 | 7 | 8 | |
|---|---|---|---|---|---|---|---|---|---|
| FALSE WOOD | GR. 1 | GR. 1 | GR. 1 | GR. 1 | GR. 1 | GR. 1 | GR. 2 | GR. 1 | ⎫ |
| KNOT | GR. 1 | GR. 1 | GR. 1 | GR. 1 | GR. 1 | GR. 1 | GR. 1 | GR. 2 | ⎬ 104 |
| CRACK | GR. 1 | GR. 1 | GR. 1 | GR. 1 | GR. 1 | GR. 1 | GR. 1 | GR. 3 | |
| ROTTEN PARTS | GR. 1 | GR. 1 | GR. 1 | GR. 1 | GR. 1 | GR. 1 | GR. 1 | GR. 1 | ⎭ |
| (SUMMARY) | GR. 1 | GR. 1 | GR. 1 | GR. 1 | GR. 1 | GR. 1 | GR. 2 | GR. 3 | |

SOLUTIONS

| | | |
|---|---|---|
| FALSE WOOD | 6 FEET GR. 1 OR 8 FEET GR. 2 (ALSO IMPLIES 7 FEET GR. 2) | ⎫ |
| KNOT | 7 FEET GR. 1 OR 8 FEET GR. 2 | ⎬ 106 |
| CRACK | 7 FEET GR. 1 OR 8 FEET GR. 3 | |
| ROTTEN PARTS | 8 FEET GR. 1 OR 8 FEET GR. 1 | ⎭ |

ELIMINATION OF SUPERIOR QUALITY SOLUTIONS FOR SAME LENGTH
AND OF SUPERIOR LENGTHS FOR SAME QUALITY

REMAINING SOLUTIONS:

| | VALUE |
|---|---|
| • 6 FEET GR. 1 | $0.96 |
| • 7 FEET GR. 2 (IMPLICATION) | $0.89 |
| • 8 FEET GR. 3 | $0.75 |

⎬ 108

• IF SELECTED CRITERIA IS FIBER RECOVERY THEN 8 FEET GR. 3 IS RETAINED  ⎫
• IF SELECTED CRITERIA IS MARKET VALUE THEN 6 FEET GR. 1 IS RETAINED  ⎬ 110

FIG. 8B

| ZONE | 1 | 2 | 3 | 4 | 5 | 6 | 7 | 8 | |
|---|---|---|---|---|---|---|---|---|---|
| FALSE WOOD | GR. 2 | GR. 1 | GR. 1 | GR. 1 | GR. 1 | GR. 1 | GR. 1 | GR. 1 | } 104 |
| KNOT | GR. 1 | GR. 1 | GR. 1 | GR. 2 | GR. 1 | GR. 1 | GR. 1 | GR. 2 | |
| CRACK | GR. 1 | GR. 1 | GR. 1 | GR. 1 | GR. 1 | GR. 1 | GR. 3 | GR. 3 | |
| ROTTEN PARTS | GR. 1 | GR. 2 | GR. 1 | GR. 1 | GR. 1 | GR. 1 | GR. 1 | GR. 1 | |
| (SUMMARY) | GR. 2 | GR. 2 | GR. 1 | GR. 2 | GR. 1 | GR. 1 | GR. 3 | GR. 3 | |

SOLUTIONS

| | | |
|---|---|---|
| FALSE WOOD | 7 FEET GR. 1 (CLOSE END) OR 8 FEET GR. 2 | } 106 |
| KNOT | 3 FEET GR. 1 OR 8 FEET GR. 2 (IMPLIES 7-6-5-4 FEET GR. 2) | |
| CRACK | 6 FEET GR. 1 OR 8 FEET GR. 3 (IMPLIES 7 FEET GR. 3) | |
| ROTTEN PARTS | 6 FEET GR. 1 (CLOSE END) OR 8 FEET GR. 2 (IMPLIES 7 FEET GR. 2) | |

ELIMINATION OF SUPERIOR QUALITY SOLUTIONS FOR SAME LENGTH
AND OF SUPERIOR LENGTHS FOR SAME QUALITY

REMAINING SOLUTIONS:

| | VALUE | |
|---|---|---|
| • 8 FEET GR. 3 | $0.75 | |
| • 7 FEET GR. 3 (IMPLICATION) | $0.68 | } 108 |
| • 6 FEET GR. 2 (IMPLICATION) | $0.70 | |
| • 5 FEET GR. 2 (IMPLICATION) | $0.25 | |
| • 4 FEET GR. 2 (IMPLICATION) | $0.15 | |

- IF SELECTED CRITERIA IS FIBER RECOVERY THEN 8 FEET GR. 3 IS RETAINED  } 110
- IF SELECTED CRITERIA IS MARKET VALUE THEN 8 FEET GR. 3 IS RETAINED

LUMBER GRADING SYSTEM

FIELD OF THE INVENTION

The present invention relates to lumber grading, and more particularly to a lumber grading system for providing a lumber cutting solution for a piece of lumber, as needed for example by a classification and trimming computer unit operating a saw machine in a sawmill.

BACKGROUND

The grading station is the cornerstone of any sawmill. It is at this station that the lumber is evaluated usually by human graders. The judgment of a grader is capital since he is responsible of attributing a grade to the piece of lumber and routing the piece according to the grade for proper classification and preparation. Once the grader has examined the piece, a mechanical conveyor system directs the piece accordingly in the production line. The decision of the grader is very important since it determines the treatment to be carried out on the piece. Cutting operations will then be performed to transform the piece of lumber into a finished product ready for distribution. The optimization of the sawmill is thus left to human judgment. If the grader judges too favourably the pieces of lumber, the customers will not receive the expected products at the quality level. Conversely, if the pieces are judged too strictly by the grader, the sawmill will sell products of good quality under the seal of second quality at lesser costs. There is thus a dilemma at this level. Each person though having the same training may have a different appreciation for a same piece of lumber. The sawmill thus largely depends on grading station since all the produced pieces must be subjected to a visual inspection. The current rate is about 50 to 60 pieces per minute per grading station. This requires intense concentration to analyse and judge one piece per second. A sawmill having only one grading station can produce no more than 60 pieces per minute. To increase production, one or two additional grading stations must be implemented. Though it seems easy to add additional grading stations, reality is quite different. In most of the sawmills, the physical space is very limited and outstanding ingenuity must be exercised to achieve such a change. Even when the physical space is appropriate, the addition of another conventional system involves high costs at the mechanical level.

The policy in the presently operating sawmills is often as follows. If the grader has a doubt on the quality of a piece, he/she must downgrade it. This causes a diminution of the value-added of the products. Maintenance costs of the complex mechanical systems and the production time losses related to the grading stations represent important costs.

Known in the art is U.S. Pat. No. 6,031,567 (Johnson) which discloses a method and an apparatus for video lumber grading, so that the human graders can work at a remote location from the lumber conveyors, in a better environment for concentration. The apparatus captures video images of lumber and displays the images to the workers who assign grades and/or cutting solutions through appropriate consoles.

Some automated grading systems have been proposed in the past, using complex image scanning and processing techniques applied on pieces of lumber travelling longitudinally over a conveyor. The prohibitive costs and the technical difficulties for implementing these systems have made them all but satisfactorily practical.

SUMMARY

An object of the invention is to provide a lumber grading system which is simple in construction and operation, takes little space and adapts to existing sawmill equipment, can process a high volume of lumber, is inexpensive, reliable and efficient.

According to the present invention, there is provided a lumber grading system for providing a lumber cutting solution for a piece of lumber, comprising:

a first camera adapted to take an image of rear and bottom sides of the piece of lumber;

a second camera adapted to take an image of front and upper sides of the piece of lumber;

a first video acquisition means connected to the first camera, for acquiring the image generated by the first camera;

a second video acquisition means connected to the second camera, for acquiring the image generated by the second camera;

a computer means connected to the first and second acquisition means, for performing an image processing of the images and generating the lumber cutting solution for the piece of lumber based on preset grade determination parameters, the image processing including a longitudinal division of the images of the piece of lumber into a number of consecutive zones based on predetermined lumber cutting positions, an attribution of respective grades to the zones based on an image analysis of the zones as a function of the preset grade determination parameters, and a solution search providing the lumber cutting solution as a function of the grades attributed to the zones; and a communication means connected to the computer means, for transmitting the lumber cutting solution.

BRIEF DESCRIPTION OF THE DRAWINGS

A detailed description of preferred embodiments will be given herein below with reference to the following drawings, in which like numbers refer to like elements.

DETAILED DESCRIPTION OF THE PREFERRED EMBODIMENTS

Figure 1:
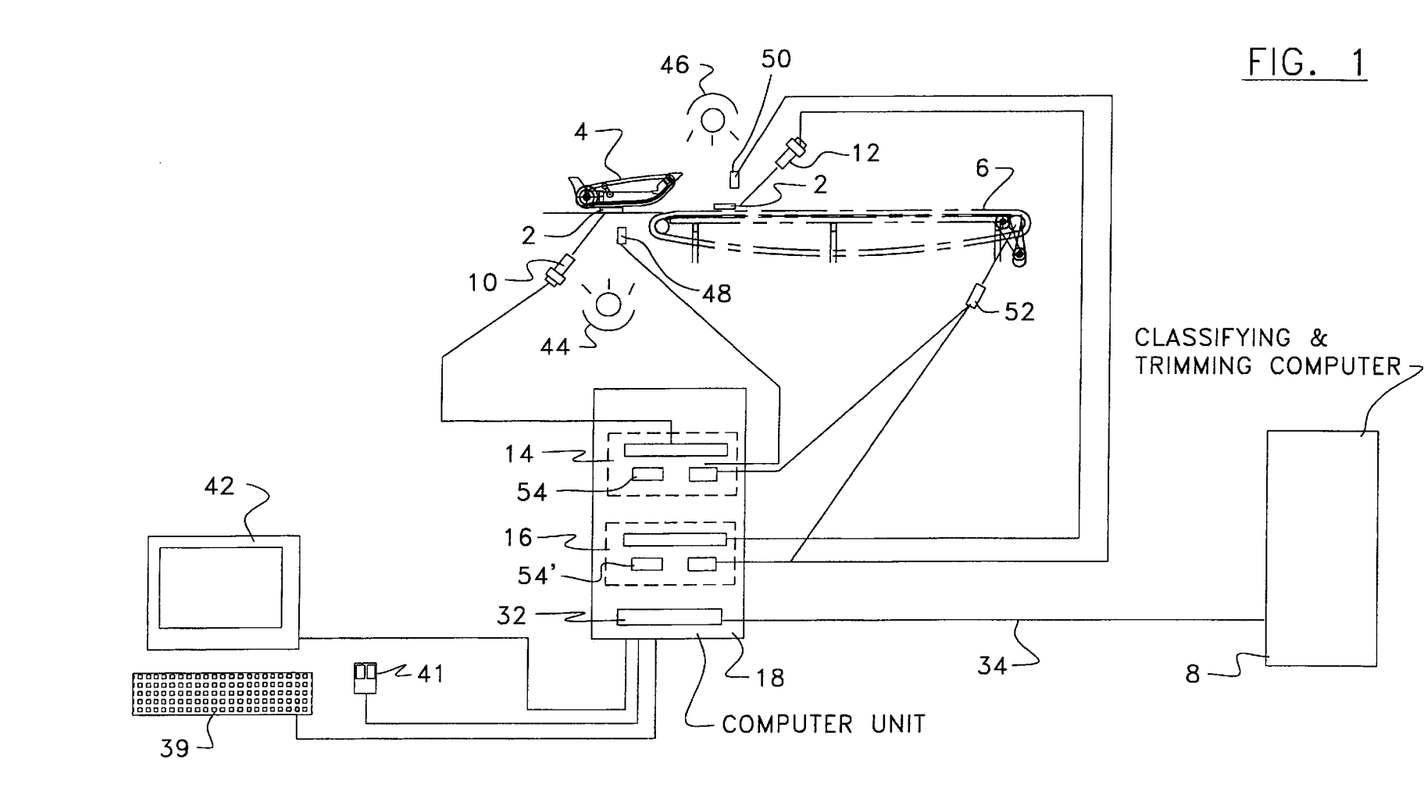
FIG. 1 is a schematic diagram illustrating a lumber grading system according to the invention.

Referring to FIG. 1, there is shown an embodiment of a lumber grading system according to the invention which, in the illustrated case, is installed at the grading station of a sawmill to provide a lumber cutting solution for each piece of lumber 2 to a classification and trimming computer 8. The pieces of lumber 2 are loaded one after another onto a conveyor arrangement that can be formed of a first lug chain 4 operating from above and a second lug chain 6 operating from below. The lumber grading system has a first camera 10 adapted to take an image of rear and bottom sides 20, 22 of the piece of lumber 2 (see FIGS. 3A–C) while it is driven by the first lug chain 4, and a second camera 12 adapted to take an image of front and upper sides 24, 26 of the piece of lumber 2 (see FIGS. 3A–C) while it is driven by the second lug chain 6. A first video acquisition circuit 14 is connected to the first camera 10, for acquiring the image that it generates. A second video acquisition circuit 16 is connected to the second camera 12, for acquiring the image that it generates. A computer unit 18 is connected to the first and second acquisition circuits 14, 16, for performing an image processing of the images and generating the lumber cutting solution for the piece of lumber 2 based on preset grade determination parameters. The first and second video acquisition circuits 14, 16 and the computer unit 18 may take various configurations, so long as they provide and perform the required functions. For example, the video acquisition circuits 14, 16 may conveniently be embodied by separate video cards as illustrated or a single video card mounted in the computer unit 18 and successively shared by the two cameras 10, 12.

Figure 5A:
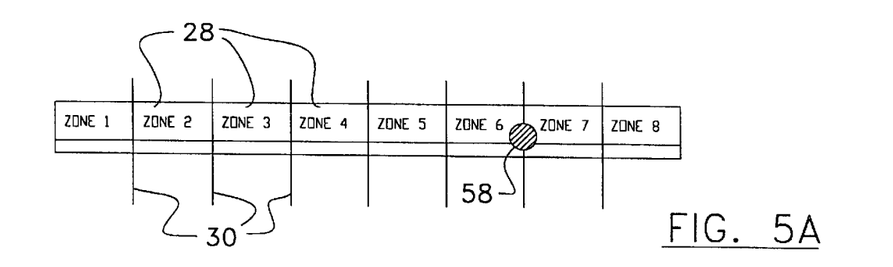
FIGS. 5A–B are schematic diagrams illustrating a shifting of the divisions of a piece of lumber according to the invention.
Figure 8A:
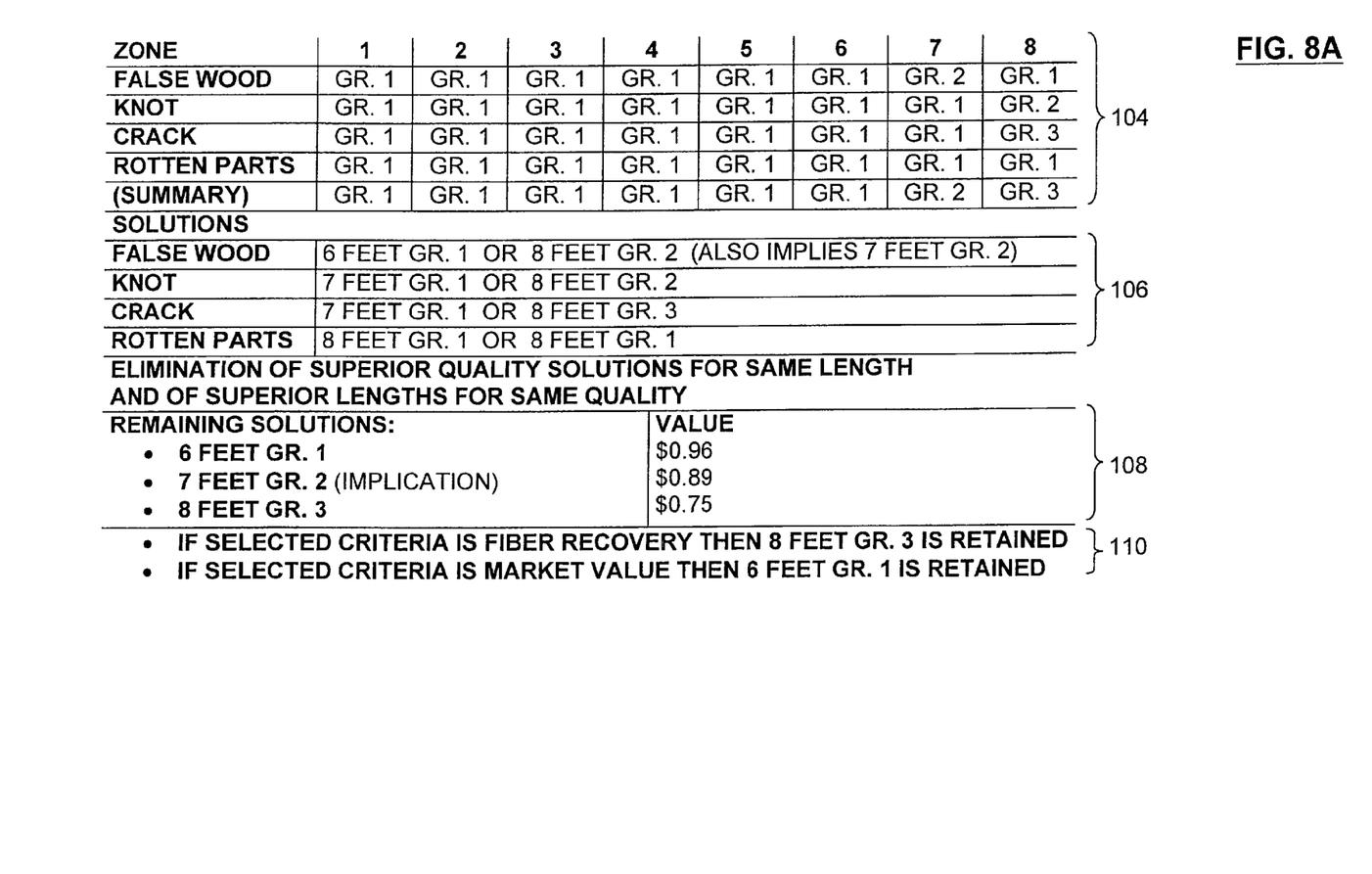
FIGS. 8A–B are schematic diagrams illustrating examples of lumber cutting solutions provided by the lumber grading system according to the invention, for pieces of lumber having different qualities.
Figure 8B:
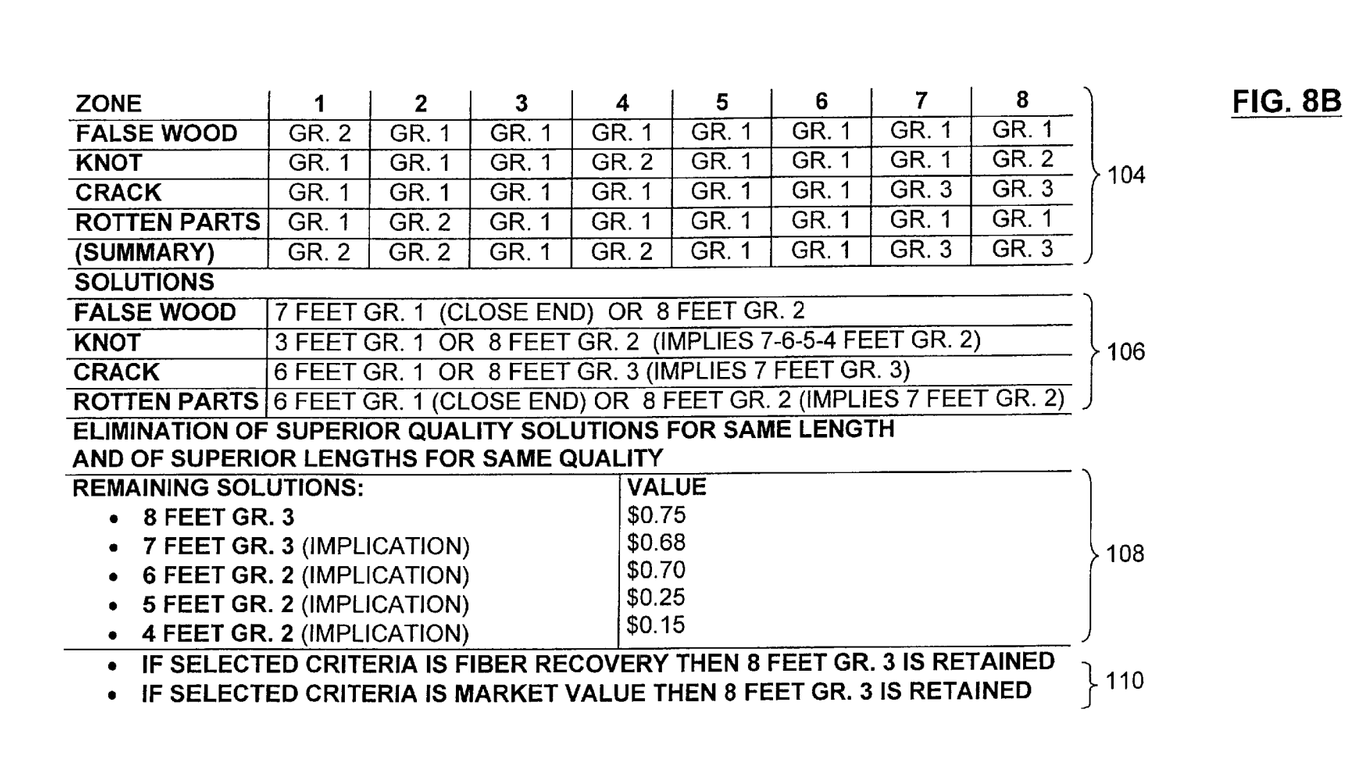

Referring to FIG. 5A, basically, the image processing performed by the computer unit 18 begins with a longitudinal division of the images of the piece of lumber 2 into a number of consecutive zones 28 based on possible lumber cutting positions 30 likely to be determined by the capabilities of the sawing or trimming unit controlled by the computer 8. Respective grades are then attributed to the zones based on an image analysis of them as a function of the preset grade determination parameters. Examples of grades attributed to the zones are shown in FIGS. 8A–B. A solution search providing the lumber cutting solution is then achieved as a function of the grades attributed to the zones 28.

Referring to FIG. 1, a communication device 32 is connected to the computer unit 18, for transmitting the lumber cutting solution. The communication device 32 can conveniently be embodied by a communication interface mounted in the computer unit 18, with a communication port connected to the classification and trimming computer 8 through any suitable communication link 34. The classification and trimming computer can be embodied for example by a Programmable Logic Controller (PLC) or an industrial computer.

The grade determination parameters preferably include predetermined lumber quality factors having respective tolerance ranges corresponding to successive grade levels, i.e grade 1, 2, 3, etc. The quality factors may consist of percentages of false wood, knots, cracks and rotten parts in the piece of lumber 2 under scrutiny, as usually considered in grading stations. The image analysis involves a detection of lumber characteristics corresponding to the lumber quality factors in each zone 28 of the images. Each one of the zones 28 is then attributed a grade for each one of the lumber quality factors based on the tolerance ranges into which the lumber characteristics fall.

Figure 3A:
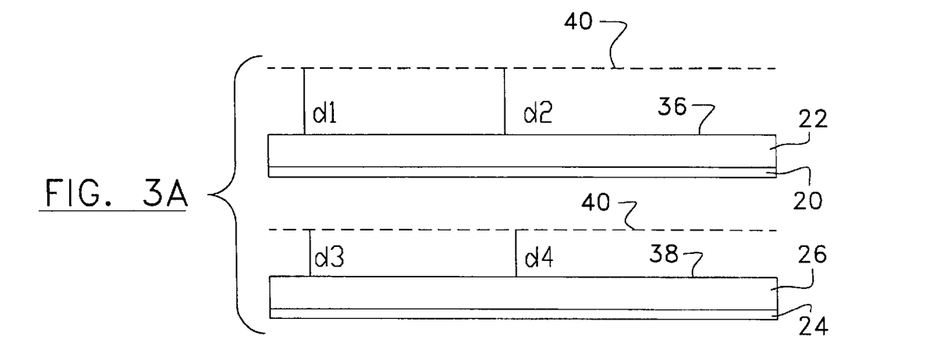
FIGS. 3A–C are schematic diagrams illustrating examples of different curvatures that can be measured by the lumber grading system according to the invention.
Figure 3B:
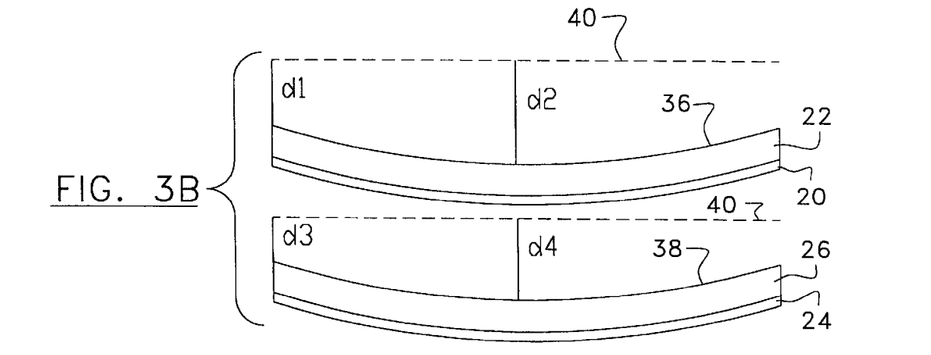
Figure 3C:
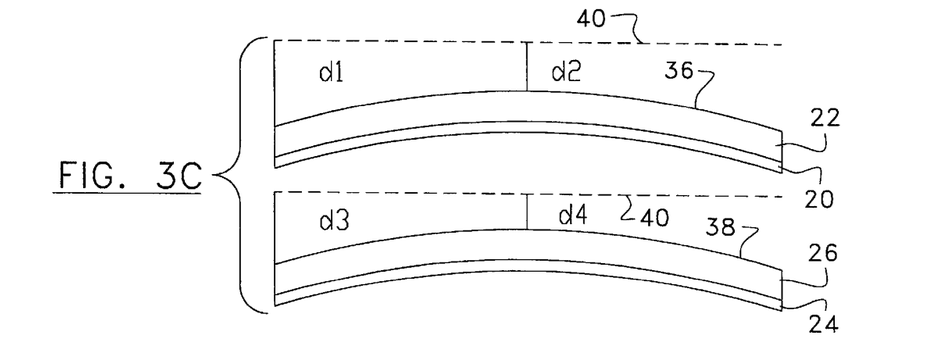

Referring to FIGS. 3A–C, the image processing also preferably involves a detection of a curvature along lumber edge lines 36, 38 in the images which can be simply done by comparing the edge lines 36, 38 with respect to a reference line 40 perpendicular to the travelling course, so that a grade is attributed to the piece of lumber 2 based on a degree of the curvature.

The solution search preferably involves, for each one of the lumber quality factors, a determination of a highest quality solution provided by a greatest number of consecutive ones of the zones 28 having a best one of the grades, and a determination of a longest lumber solution provided by a greatest number of consecutive ones of the zones 28 having a lesser one of the grades. An elimination of the solutions of higher quality for a same length and the solutions of higher length for a same quality is then achieved. A selection of a best one of the solutions remaining after the elimination is further performed as a function of a user-selected factor 86. The lumber cutting solution is then set as a function of the best one of the solutions. The user-selected factor 86 may be a highest market value or a wood fiber recovery quantity.

The computer unit 18 is preferably provided with input and display devices like a keyboard 39, a mouse 41 and a screen 42 for inputting and displaying the grade determination parameters and the user-selected factor.

Figure 6A:
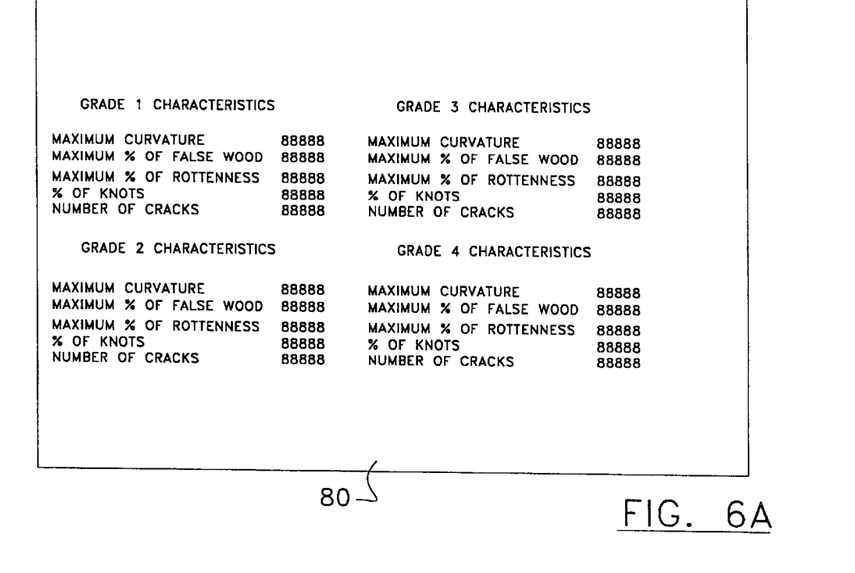
FIGS. 6A–B are schematic diagrams illustrating examples of user interfaces for setting and adjusting grading and lumber cutting solution parameters.
Figure 6B:
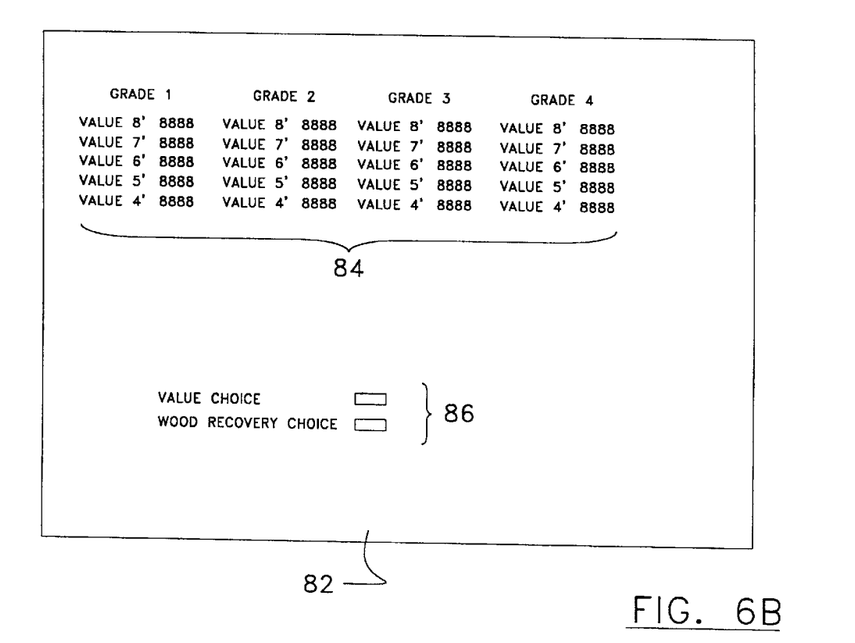

As shown in FIGS. 6A–B, a first user-friendly display interface 80 can be used to adjust the various parameters for each grade. This can be done by inputting, for each grade, the maximum allowed degree of curvature, the maximum allowed percentages of false wood, rotten parts and knots, the maximum allowed number of cracks. A second display interface 82 can be used for inputting pricing information 84 for possible lengths of pieces of lumber as a function of the grades, and for inputting the user-selected factor 86 so that the cutting solution is based either on the highest price that can be obtained for the piece of lumber 2 once cut if necessary, or the quantity of wood (fiber) that can be recovered for an acceptable grade level.

First and second lighting sources 44, 46 respectively directed over and under the piece of lumber 2 toward target areas viewed by the cameras 10, 12, are preferably used to increase contrasts in the images captured by the cameras 10, 12.

The synchronization and timing of the cameras 10, 12 with the conveyor arrangement can be achieved using detectors 48, 50 connected respectively to the computer unit 18, to detect when the piece of lumber 2 reaches predetermined points along a travelling course followed by the piece of lumber 2 in a sideways direction. The detectors 48, 50 can conveniently be embodied by low voltage detection photocells operating for example between 5 and 10 volts. An encoder 52 suitably installed on the lug chain 6 and connected to the computer unit 18 may be used to provide positional information on the piece of lumber 2 along the travelling course. The encoder 52 may be of a type that produces pulses in response to rotation. The computer unit 18 can then properly process the images acquired by the cameras 10, 12 in response to the detectors 48, 50 and as a function of the information provided by the encoder 52.

The cameras 10, 12 can conveniently be embodied by digital line scan cameras respectively directed over and under the travelling course at an angle therewith and toward spaced apart upstream and downstream target areas along the travelling course. The line scan cameras preferably have longitudinal fields of vision on the piece of lumber 2. Line scan cameras having a line resolution of 4096 or 2048 pixels may be used for that purpose. Preferably, the angle of the cameras will be 45° with respect to the conveyor arrangement so that the dimensions of the sides of the piece of lumber 2 are true in the captured images. Otherwise, a correction would be required as a function of the angle of the cameras 10, 12. The computer unit 18 performs an assembly of lines scanned by the line scan cameras and acquired by the video acquisition circuits 14, 16 in response to the detectors 48, 50 and as a function of the positional information provided by the encoder 52 for line synchronization, in order to build the images. The computer unit 18 may be provided with a memory 54 for temporary storage of the image resulting from the assembly of the lines provided by the camera 10 directed toward the upstream target area, until the image resulting from the assembly of the lines provided by the camera 12 directed toward the downstream target area is obtained. The computer unit 18 can then assemble the images together to proceed with the analysis of the images in the assembled form. Gain and offset adjustments of the cameras 10, 12 may be performed through the computer unit 18 suitably linked to the cameras 10, 12 for this purpose (not shown in the Figures).

Referring to FIGS. 3A–C, the detection of the curvature may be achieved by a measurement of minimum and maximum distances d1, d2 between the lumber edge lines 36, 38 in the images and the reference line 40 over a predetermined length of the piece of lumber 2, e.g. by a number of distance measurements achieved over half the length of the piece provided that the curvature is constant over the whole length, and a subtraction between the maximum and minimum distances d1, d2. The degree of the curvature of the piece of lumber 2 is then determined as a function of a result of the subtraction.

Figure 4A:
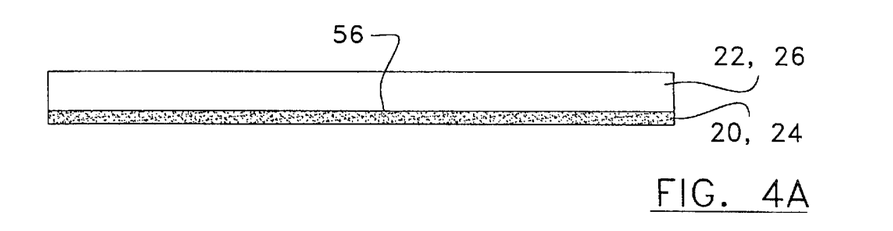
FIGS. 4A–B are schematic diagrams illustrating the brightness difference between a piece of lumber with (5B) and without (5A) false wood, according to the invention.
Figure 4B:
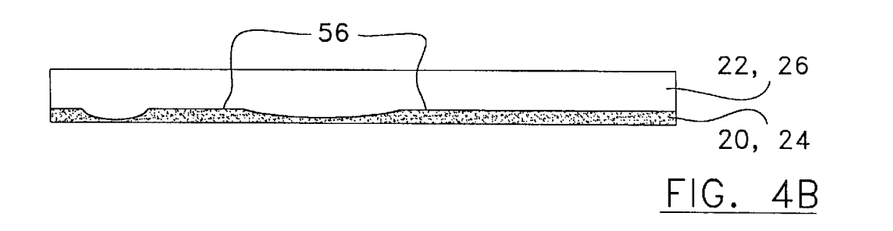

Referring to FIGS. 4A–B, the detection of the lumber characteristics in relation with the percentage of false wood may be achieved by a detection of discontinuities in straight lines 56 demarcating the bottom and upper sides 22, 26 from the rear and front sides 20, 24 respectively, resulting from different brightness between the sides 20, 22, 24, 26 in the images, as exemplified in FIGS. 4A–B (without and with false wood respectively).

The detection of the lumber characteristics in relation with the percentages of knots, cracks and rotten parts may be achieved by a detection of a number and extent of darker areas in the images with respect to a predetermined reference brightness.

Figure 5B:
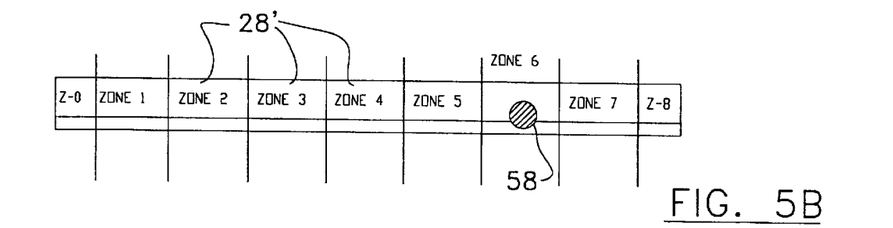

Referring to FIGS. 5A–B, the image analysis preferably further involves, prior to the solution search and after the attribution of the grades, a shifting of the zones 28 in a longitudinal direction of the piece of lumber 2 by a half-width of the zones 28 (result is shown in FIG. 5B). A new detection of the lumber characteristics in the shifted zones 28' is then achieved with each one of the zones 28' being attributed again a grade for each one of the lumber quality factors depending on the lumber characteristics detected by the new detection. A downgrading of the grades formerly attributed to successive ones of the zones 28 happens when the grade attributed to the zone 28', once shifted, that falls inside the successive ones of the zones 28, corresponds to an addition of the grades formerly attributed to the successive ones of the zones 28 before the shifting, for each one of the lumber quality factors. Such an operation allows to determine whether a defect is located directly on a lumber cutting position 30 dividing two successive zones 28, in which case both affected zones 28 must be downgraded in relation with the kind of defect. For example, as illustrated, the piece of lumber 2 has a rotten portion 58 located on the cutting position 30 between zones 6 and 7. As a result of the image analysis, zones 6 and 7 could possibly have 15% and 10% of rottenness respectively. At that time, however, there is no indication on whether the rottenness is distributed over the zones or concentrated at a cutting position. By shifting the zones 28' as shown in FIG. 5B, then the percentage of rottenness detected in new zone 6 (falling between the former zones 6 and 7) will amount to 25% (the sum of the former measurements), meaning that the defect is indeed located on the cutting position. Otherwise, a different percentage would likely be obtained.

Figure 2:
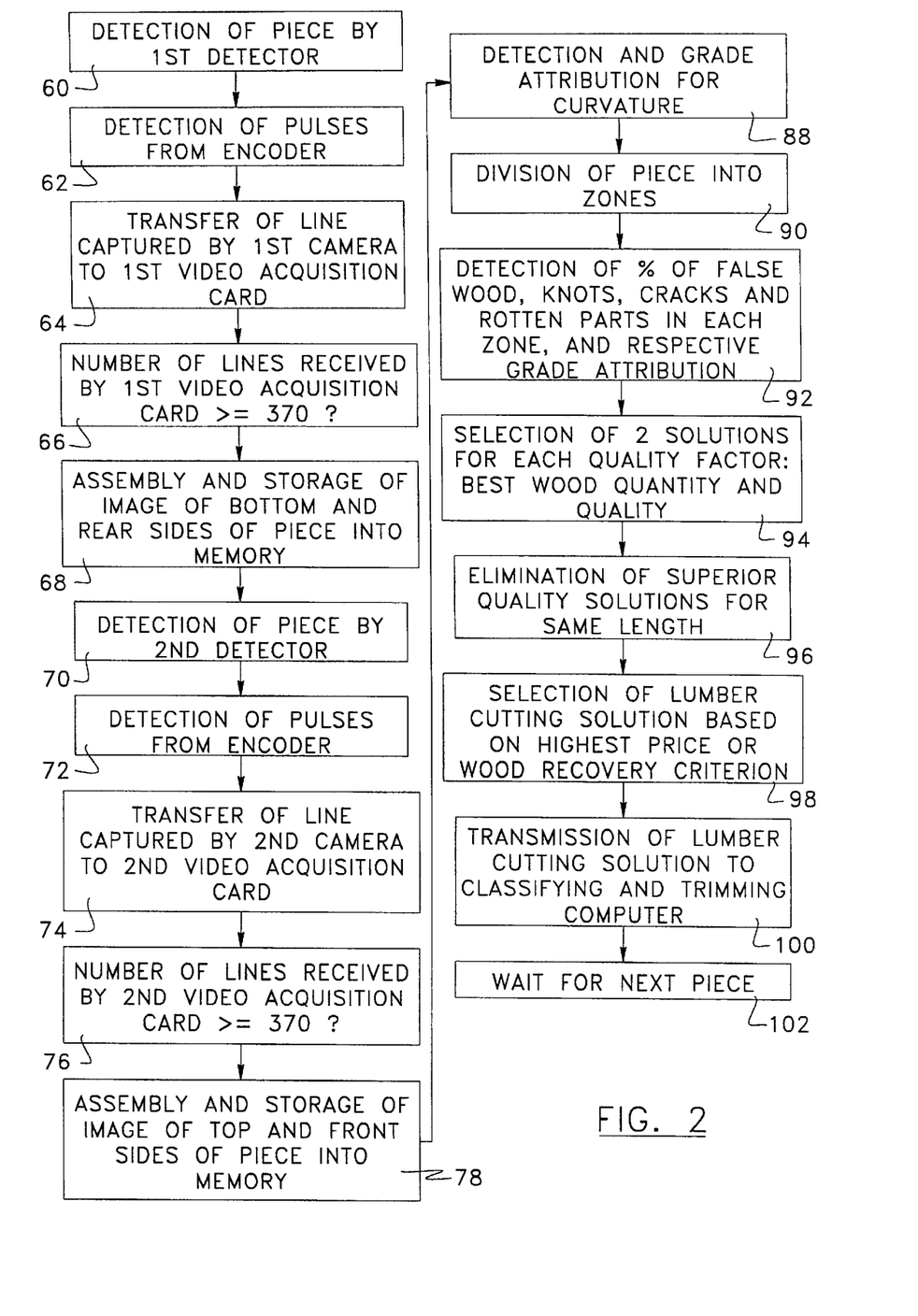
FIG. 2 is a flowchart illustrating operations performed by the lumber grading system according to the invention.

Referring to FIGS. 1 and 2, in operation, as depicted by block 60, the piece of lumber 2 will be first detected by the detector 48 once it reaches a predetermined position along the travelling course covered by the lug chain 4. The signal produced by the detector 48 indicates that the computer unit 18 can begin to assemble the lines captured by the first camera 10 in order to form the image of the bottom and the rear side of the piece of lumber 2. As depicted by block 62, the pulses produced by the encoder 52 provide a signal used for the synchronization of the lines. As depicted by block 64, each line captured by the first camera 10 is transmitted to the first video acquisition card 14, until a predetermined number of lines is acquired, e.g. 370 lines as depicted by block 66. The image is then complete and is temporarily stored in memory 54. As depicted by blocks 70–78, the same process is repeated while the piece of lumber 2 travels on the lug chain 6 and is detected by the detector 50, the camera 12 being then used to transmit lines to the second video acquisition circuit 16 in order to form an image of the front and top sides of the piece of lumber 2 which can be equally stored into memory 54'. From this moment, the computer unit 18 may retrieve the two images stored in memory 54, 54' and combine them into a single image of the four faces of the piece of lumber 2 (in an "unfolded" view) for the subsequent image analysis operations.

Figure 7A:
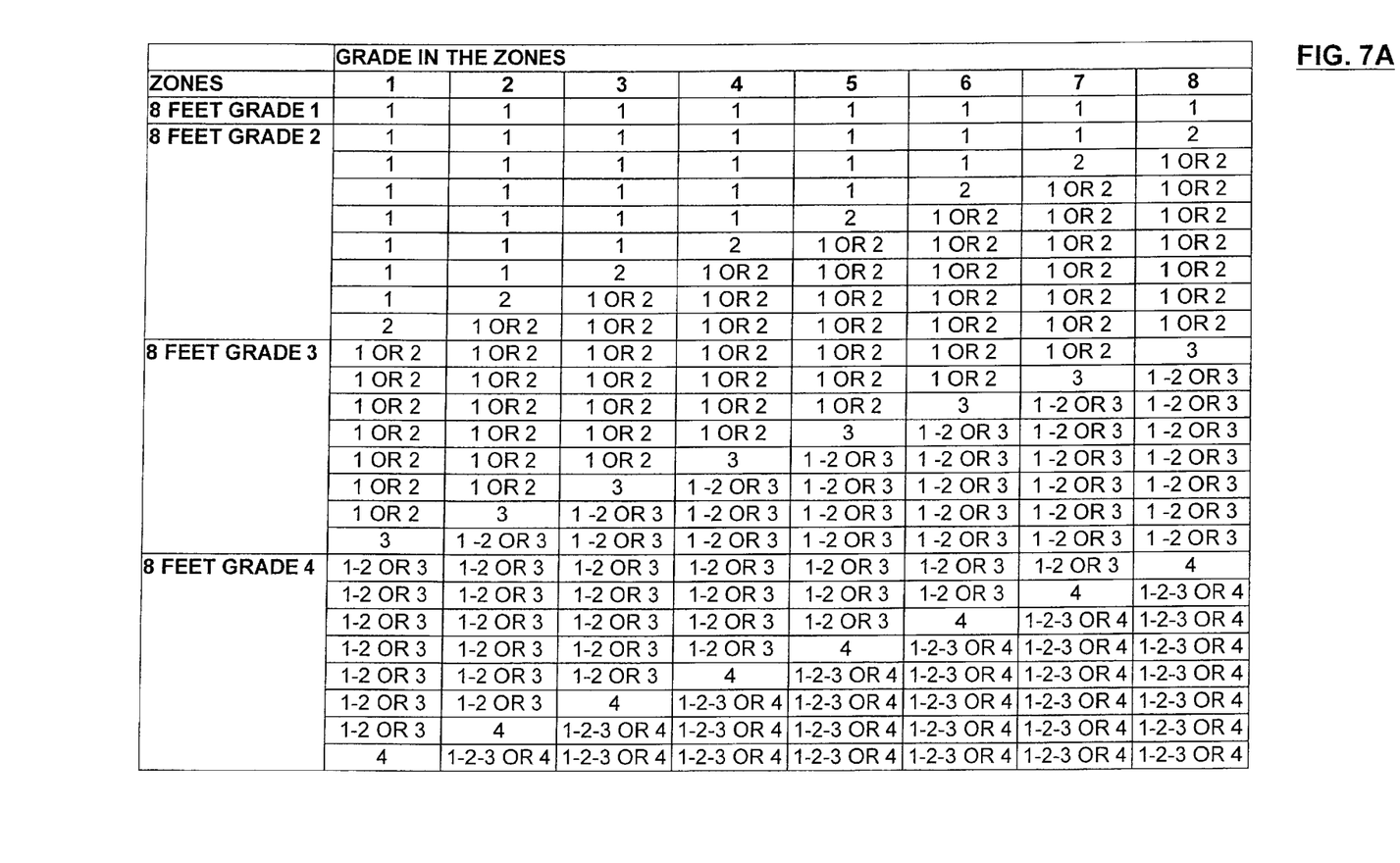
FIGS. 7A–E are examples of lumber classification tables used by the lumber grading system according to the invention.
Figure 7B:
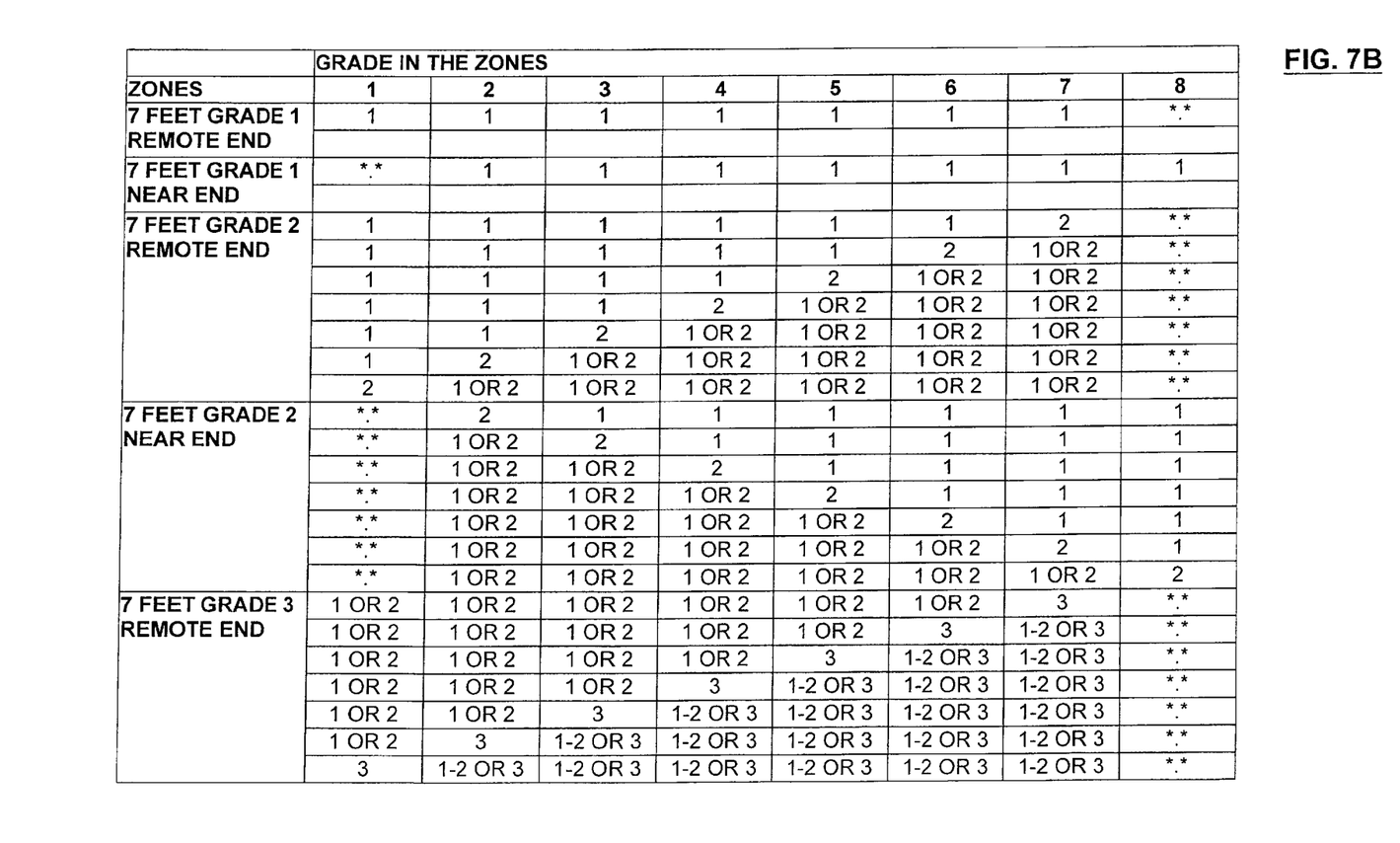
Figure 7C:
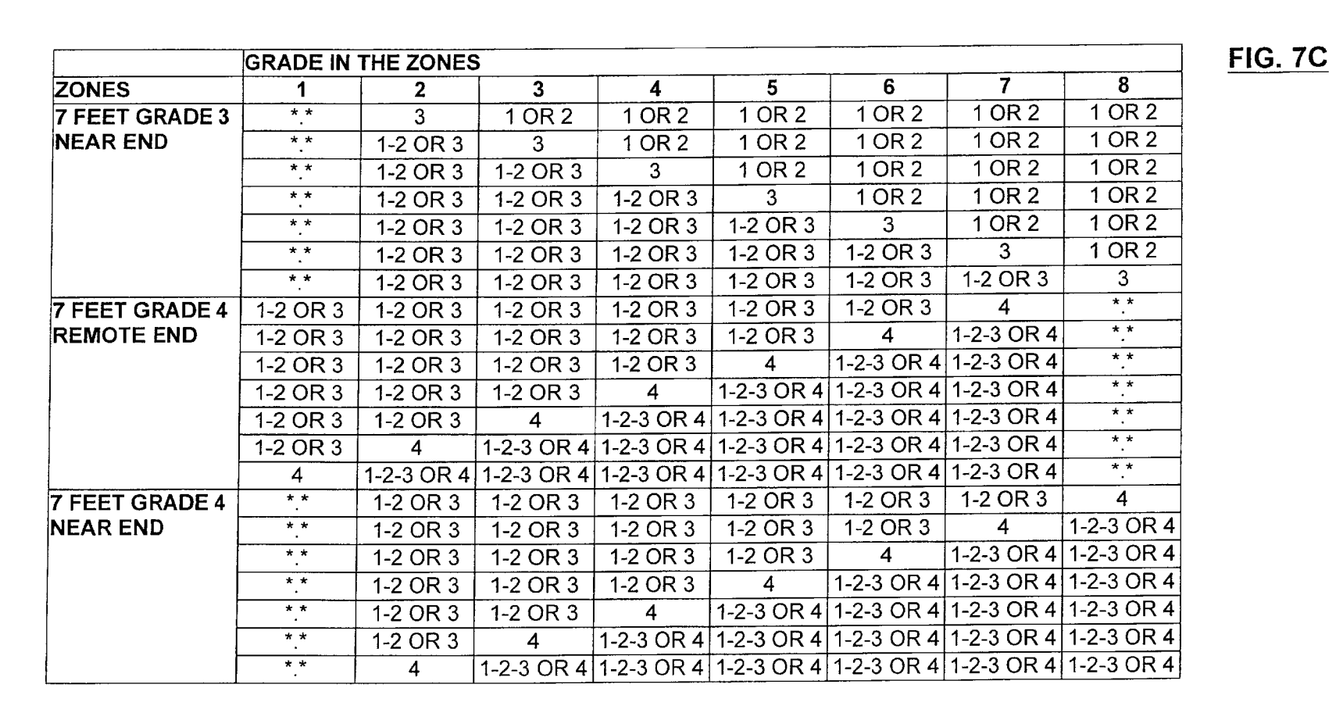
Figure 7D:
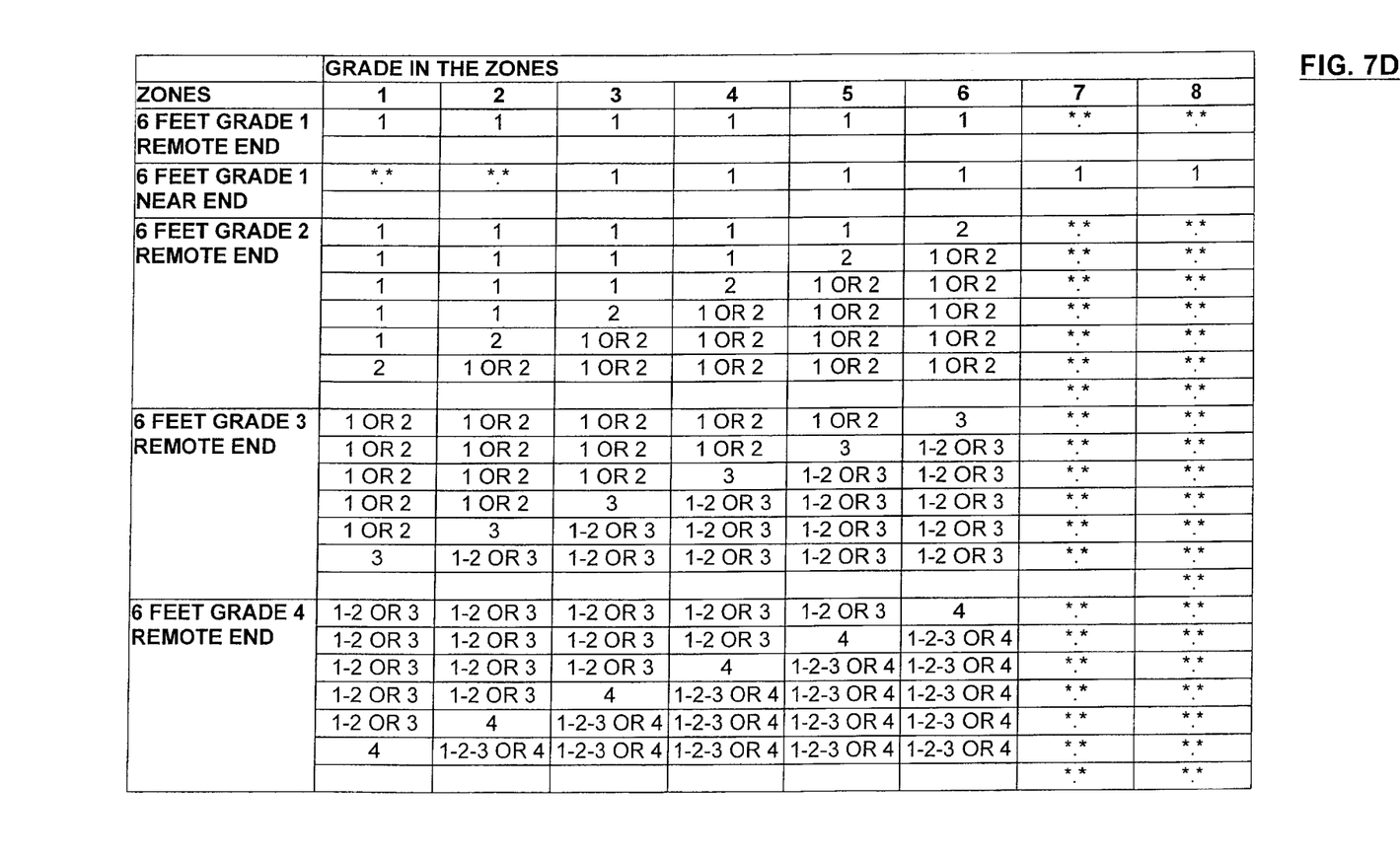
Figure 7E:
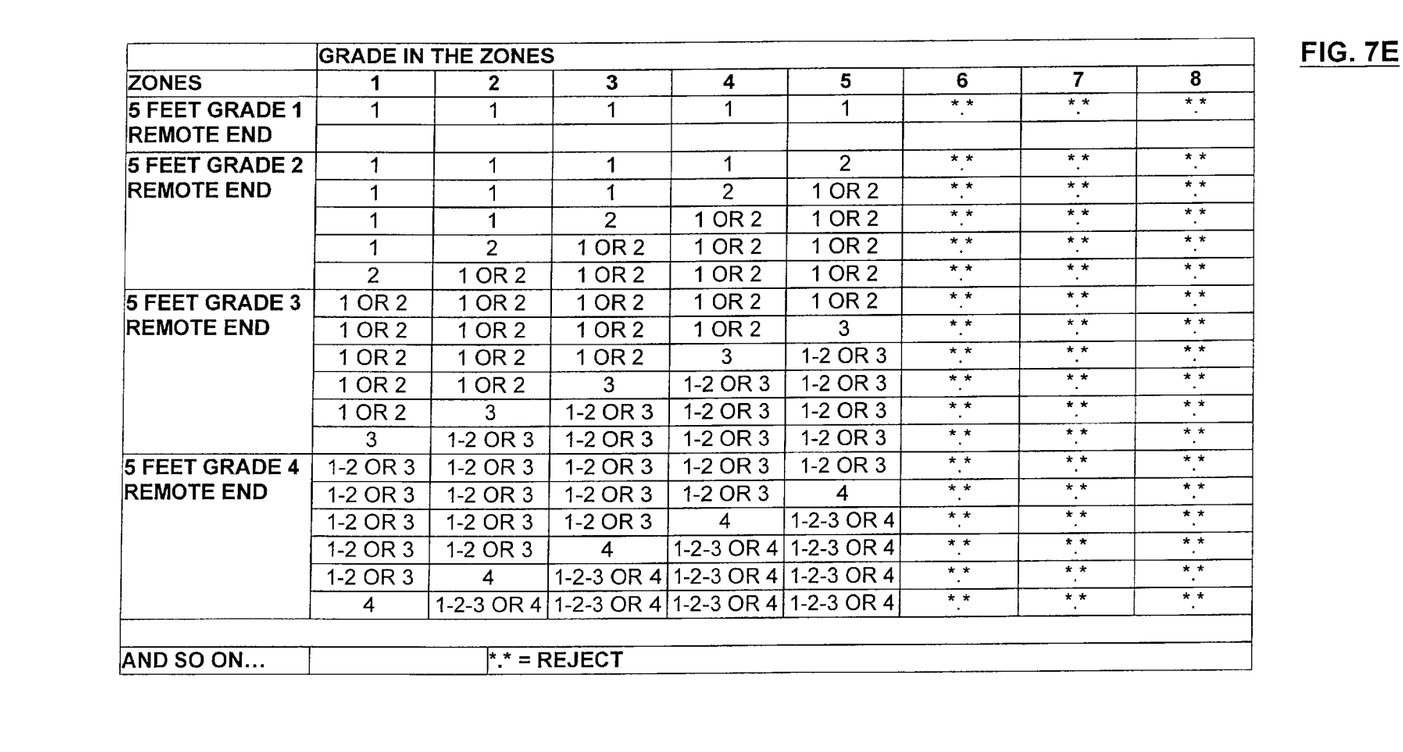

As depicted by block 88, the image analysis may begin with a detection of a possible curvature of the piece of lumber 2. The computer unit 18 attributes a curvature-related grade to the piece of wood based on the degree of curvature so detected and the maximum allowed curvature entered by the user for each grade (see FIG. 7A). If the degree of curvature exceeds an acceptable level, then the piece of lumber 2 is classified as a reject. The cameras 10, 12 should have at least a certain angle with respect to the lumber travelling course in order to see the curvature in the piece of lumber 2. Referring to FIGS. 3A–C, the curvature is measured by superimposing in the image a reference line 40 which is as perpendicular as possible with respect to the lumber travelling course or, otherwise, is parallel with the longitudinal orientation of the piece of wood when it travels on the conveyor arrangement. A series of pixel measurements is taken over a significant length of the piece of lumber, e.g. half its length, between an edge 36, 38 of the lumber and the reference line 40. A subtraction is achieved between the maximum and the minimum number of pixels so measured and the degree of curvature is established based on the result of the subtraction.

As depicted by block 90, the computer unit 18 then proceeds with a division of the piece of lumber into zones 28 as shown in FIG. 6A. Each zone 28 is then attributed a false wood-related grade, a rotten part-related grade, a knot-related grade, and a crack-related grade as depicted by block 92. The false wood is determined from a difference in the brightness between the sides in the images, which can be enhanced by the lighting sources 44, 46. FIG. 4A shows a perfect piece of wood where the bottom and top sides 22, 26 are brighter than the front and rear sides 20, 24 due to the angle of the lighting sources 44, 46, with a straight brightness demarcation between the sides. FIG. 4B shows a piece of lumber having false wood which clearly appears under the form of an irregular brightness line between the sides.

As knots, rotten parts and cracks appear darker in the images, they can be easily detected by using for example cameras 10, 12 that provide grey level information, e.g. 256 shades of grey over 8 bits. It is then just a matter of detecting the number, extent (shape) and grey level of the darker zones in the image to determine whether they represent cracks, knots or rotten parts and their respective percentages. The zone shifting process as formerly described above is preferably performed to detect possible defects located over cutting lines and to adjust the grades of the zones divided by the cutting lines accordingly.

As depicted by block 94, a solution search then begins based on the grades attributed to each zone for each quality factor. For this purpose, lumber classification tables like those illustrated in FIGS. 7A–E can be implemented in the computer unit 18 to determine the possible respective lengths and grades in which the piece of lumber can be classified based on the grades attributed to each zone for each quality factor.

As depicted by block 96, the superior quality solutions for a same length in view of all the quality factors are then eliminated as the overall quality of a piece of lumber will always depend on the worst defect.

As depicted by block 98, a single cutting solution is selected among the remaining solutions based on the user-inputted criteria 86, i.e. highest market value (price) or highest wood recovery quantity (see FIG. 6B). The lumber cutting solution is transmitted to the classifying and trimming computer 8, as depicted by block 100, and the computer unit 18 then waits for the next piece of lumber to process as depicted by block 102.

FIG. 8A shows a first example of how a lumber cutting solution can be determined by the computer unit 18 as a function of grades 104 attributed to the zones of a given piece of lumber. Using the tables shown in FIGS. 7A–E, two solutions 106 are retained for each quality factor. As it can be seen on the solution line in respect with the false wood, additional solutions can be implied as, for example, a 7 feet grade 2 lumber product can of course be obtained by cutting one feet of an 8 feet grade two lumber product, and so on. Once the superior quality solutions for a same length and the solutions of superior lengths for a same quality are eliminated, there remain three solutions 108, one of which derives from an implied solution at the former level of the solution search. The selected lumber cutting solution 110 is ultimately based on the user-selected criteria.

FIG. 8B shows another example, in which the solution search is adapted to the case where a sawmill equipment is capable of performing a cutting operation on either end of the piece of lumber under process.

While embodiments of this invention have been illustrated in the accompanying drawings and described above, it will be evident to those skilled in the art that changes and modifications may be made therein without departing from the essence of this invention. All such modifications or variations are believed to be within the scope of the invention as defined by the claims appended hereto.

What is claimed is:

1. A lumber grading system for providing a lumber cutting solution for a piece of lumber, comprising:
   a first camera adapted to take an image of rear and bottom sides of the piece of lumber;
   a second camera adapted to take an image of front and upper sides of the piece of lumber;
   a first video acquisition means connected to the first camera, for acquiring the image generated by the first camera;
   a second video acquisition means connected to the second camera, for acquiring the image generated by the second camera;
   a computer means connected to the first and second acquisition means, for performing an image processing of the images and generating the lumber cutting solution for the piece of lumber based on preset grade determination parameters, the image processing including a longitudinal division of the images of the piece of lumber into a number of consecutive zones based on predetermined lumber cutting positions, an attribution of respective grades to the zones based on an image analysis of the zones as a function of the preset grade determination parameters, and a solution search providing the lumber cutting solution as a function of the grades attributed to the zones; and
   a communication means connected to the computer means, for transmitting the lumber cutting solution.

2. The lumber grading system according to claim 1, wherein:
   the grade determination parameters include predetermined lumber quality factors having respective tolerance ranges corresponding to successive grade levels;
   the image analysis includes a detection of lumber characteristics corresponding to the lumber quality factors in each zone of the images, each one of the zones being attributed a grade for each one of the lumber quality factors based on the tolerance ranges into which the lumber characteristics fall.

3. The lumber grading system according to claim 2, wherein the image analysis includes, prior to the solution search and after the attribution of the grades, a shifting of the zones in a longitudinal direction of the piece of lumber by a half-width of the zones, a new detection of the lumber characteristics in the zones with each one of the zones being attributed again a grade for each one of the lumber quality factors depending on the lumber characteristics detected by the new detection, and a downgrading of the grades formerly attributed to successive ones of the zones when the grade attributed to the zone, once shifted, that falls inside the successive ones of the zones, corresponds to an addition of the grades formerly attributed to the successive ones of the zones before the shifting, for each one of the lumber quality factors.

4. The lumber grading system according to claim 2, wherein the image processing includes a detection of a curvature along lumber edge lines in the images with respect to a reference line, a grade being attributed to the piece of lumber based on a degree of the curvature.

5. The lumber grading system according to claim 4, wherein the detection of the curvature comprises a measurement of minimum and maximum distances between the lumber edge lines in the images and the reference line over a predetermined length of the piece of lumber, and a subtraction between the maximum and minimum distances, the degree of the curvature of the piece of lumber being determined as a function of a result of the subtraction.

6. The lumber grading system according to claim 4, wherein the quality factors comprise percentages of false wood, knots, cracks and rotten parts in the piece of lumber under scrutiny.

7. The lumber grading system according to claim 6, wherein the detection of the lumber characteristics in relation with the percentage of false wood includes a detection of discontinuities in straight lines demarcating the bottom and upper sides from the rear and front sides respectively, resulting from different brightness between the sides in the images.

8. The lumber grading system according to claim 6, wherein the detection of the lumber characteristics in relation with the percentages of knots, cracks and rotten parts includes a detection of a number and extent of darker areas in the images with respect to a predetermined reference brightness.

9. The lumber grading system according to claim 6, wherein the solution search includes:
   for each one of the lumber quality factors, a determination of a highest quality solution provided by a greatest number of consecutive ones of the zones having a best one of the grades, and a determination of a longest lumber solution provided by a greatest number of consecutive ones of the zones having a lesser one of the grades;
   an elimination of the solutions of higher quality for a same length and the solutions of higher length for a same quality; and
   a selection of a best one of the solutions remaining after the elimination as a function of a user-selected factor, the lumber cutting solution being set as a function of the best one of the solutions.

10. The lumber grading system according to claim 9, wherein the user-selected factor comprises one of a highest market value and a wood recovery quantity.

11. The lumber grading system according to claim 10, wherein the computer means is provided with input and a display means for inputting and displaying the grade determination parameters and the user-selected factor.

12. The lumber grading system according to claim 1, further comprising first and second lighting means respectively directed over and under the piece of lumber toward target areas viewed by the cameras, for increasing contrasts in the images.

13. The lumber grading system according to claim 1, further comprising detectors connected respectively to the computer means, and detecting when the piece of lumber reaches predetermined points along a travelling course followed by the piece of lumber in a sideways direction, and an encoder connected to the computer means, and providing positional information on the piece of lumber along the travelling course, the computer means processing the images acquired by the cameras in response to the detectors and as a function of the positional information provided by the encoder.

14. The lumber grading system according to claim 13, wherein:
   the cameras are line scan cameras respectively directed over and under the travelling course at an angle therewith and toward spaced apart upstream and downstream target areas along the travelling course, the line scan cameras having longitudinal fields of vision on the piece of lumber; and
   the computer means further performs an assembly of lines scanned by the line scan cameras and acquired by the video acquisition means in response to the detectors and as a function of the positional information provided by the encoder for line synchronization, the images being provided by the assembly, the computer means being provided with a memory for temporary storage of the image resulting from the assembly of the lines provided by the line scan camera directed toward the upstream target area, until the image resulting from the assembly of the lines provided by the line scan camera directed toward the downstream target area is obtained, the computer means then assembling the images together and performing the processing of the images in an assembled form.

15. The lumber grading system according to claim 14, wherein:
   the grade determination parameters include predetermined lumber quality factors having respective tolerance ranges corresponding to successive grade levels;
   the image analysis includes a detection of lumber characteristics corresponding to the lumber quality factors in each zone of the images, each one of the zones being attributed a grade for each one of the lumber quality factors based on the tolerance ranges into which the lumber characteristics fall.

16. The lumber grading system according to claim 15, wherein the image processing includes a detection of a curvature along lumber edge lines in the images with respect to a reference line substantially perpendicular to the travelling course, a grade being attributed to the piece of lumber based on a degree of the curvature.

17. The lumber grading system according to claim 16, wherein the quality factors comprise percentages of false wood, knots, cracks and rotten parts in the piece of lumber under scrutiny.

18. The lumber grading system according to claim 11, wherein the solution search includes:
   for each one of the lumber quality factors, a determination of a highest quality solution provided by a greatest number of consecutive ones of the zones having a best one of the grades, and a determination of a longest lumber solution provided by a greatest number of consecutive ones of the zones having a lesser one of the grades;
   an elimination of the solutions of higher quality for a same length and the solutions of higher length for a same quality; and
   a selection of a best one of the solutions remaining after the elimination as a function of a user-selected factor, the lumber cutting solution being set as a function of the best one of the solutions.

19. The lumber grading system according to claim 18, wherein the user-selected factor comprises one of a highest market value and a wood recovery quantity.

20. The lumber grading system according to claim 19, wherein the computer means is provided with input and a display means for inputting and displaying the grade determination parameters and the user-selected factor.

21. The lumber grading system according to claim 20, further comprising first and second lighting means respectively directed over and under the piece of lumber toward target areas viewed by the cameras, for increasing contrasts in the images.

* * * * *